(12) United States Patent
Buttmann et al.

(10) Patent No.: US 7,979,227 B2
(45) Date of Patent: Jul. 12, 2011

(54) CALIBRATION IN A LABORATORY REFERENCE METHOD

(75) Inventors: Marc Buttmann, Duesseldorf (DE); Philipp Roth, Leonberg (DE); Ralf Hüsges, Leverkusen (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 30 days.

(21) Appl. No.: 12/086,701

(22) PCT Filed: Dec. 13, 2006

(86) PCT No.: PCT/EP2006/069639
§ 371 (c)(1),
(2), (4) Date: Nov. 26, 2008

(87) PCT Pub. No.: WO2007/074065
PCT Pub. Date: Jul. 5, 2007

(65) Prior Publication Data
US 2009/0145195 A1 Jun. 11, 2009

(30) Foreign Application Priority Data
Dec. 23, 2005 (DE) .......................... 10 2005 062 388

(51) Int. Cl.
*G01D 18/00* (2006.01)
*G01D 21/00* (2006.01)
(52) U.S. Cl. ........................................................ 702/85
(58) Field of Classification Search .................. 702/85
See application file for complete search history.

(56) References Cited

U.S. PATENT DOCUMENTS

| | | | |
|---|---|---|---|
| 5,511,408 A * | 4/1996 | Yoshioka et al. | 73/1.03 |
| 6,275,717 B1 * | 8/2001 | Gross et al. | 600/345 |
| 6,281,499 B1 * | 8/2001 | Kobayashi et al. | 250/339.09 |
| 6,281,818 B1 * | 8/2001 | Miller | 341/120 |
| 6,582,963 B1 * | 6/2003 | Weigl et al. | 436/52 |
| 6,629,041 B1 | 9/2003 | Marbach | |
| 2001/0013488 A1 * | 8/2001 | Fukunaga et al. | 210/85 |
| 2002/0165684 A1 * | 11/2002 | Olson | 702/85 |

FOREIGN PATENT DOCUMENTS
EP 0 660 114 B1 7/2001

* cited by examiner

*Primary Examiner* — Cindy Hien-Dieu Khuu
(74) *Attorney, Agent, or Firm* — Bacon & Thomas, PLLC

(57) ABSTRACT

In a method for calibrating a measuring device, a signal of a first sensor is mapped to a measured value based on a mapping specification. A current measured value of the measuring device is recorded as current calibration measured value; a laboratory reference sample of the measured medium with properties of the calibrated measured value at the point in time of the recording is supplied to a laboratory reference measuring device; the actual value of the measured variable is ascertained based on the laboratory reference sample and made available and recorded as current laboratory reference measured value; and, based on the current calibration measured value, as well as the current laboratory reference measured value, the mapping specification is updated. At least one earlier value pair of a calibration measured value and an associated laboratory reference measured value ascertained in an earlier calibration is considered in updating the mapping specification.

10 Claims, 2 Drawing Sheets

CALIBRATION IN A LABORATORY REFERENCE METHOD

TECHNICAL FIELD

The present invention relates to a method for calibrating a measuring device in the laboratory, and to an apparatus that implements such method.

BACKGROUND DISCUSSION

Measuring devices, especially analytical devices, such as turbidity sensors for examining aqueous media or other samples, usually include at least a first sensor for a measured variable. The signal of such sensor is mapped according to a mapping specification to an output, measured value. The mapping specification can comprise, for example, a constant factor, a linear equation, a polynomial, or some other expression. Besides depending on the signal of the first sensor, the mapping specification can also depend on signals of at least a second sensor, in order, to compensate, for example, cross-sensitivity of the first sensor to the measured variable of the second sensor, for example temperature. The mapping specification is representable, for example, in the form of characteristic curves. The parameters of the mapping specification, for example coefficients and zero-point offset, are usually stored in a data memory of the measuring device.

Ordinarily, a measuring device is calibrated at the point in time when it is put in service, so that the stored parameters of the mapping specification agree with the required parameters, to an extent such that the output measured values are the same as the actual values of the measured variable, within the desired accuracy of measurement.

Measuring devices are subject, however, to drift—i.e., due to wear, aging, fouling or other causes, the output measured value changes from the actual value of the measured variable. In this case, then the stored parameters of the mapping specification are no longer up-to-date and must be made current by a re-calibration.

For pH measuring devices, this is done, for example, by performing measurements at two different pH values with two standard liquids and by so adjusting zero-point and slope of the measuring device on the basis of the output measured values, that the measuring device outputs the correct measured values for the reference liquids.

This manner of proceeding cannot be used, for example, for fixedly installed, turbidity measuring devices for the monitoring of drinking water, since it is not practical to take these out of the drinking water and subject them to standard samples of defined degree of turbidity.

Instead of this, these turbidity measuring devices are calibrated in the so-called laboratory reference method. For this, the current measured value at the point in time of a calibration measurement is stored as calibration measured value. Simultaneously, a sample of the medium is taken and a laboratory reference measurement is performed in the laboratory on the taken sample. The result of the laboratory reference measurement is used as laboratory reference measured value for calibrating the measuring device.

From the difference between calibration measured value and laboratory reference measured value, one obtains the current deviation of the measuring device at the laboratory reference measured value. Lacking further information, this deviation is usually associated with a zero point displacement and the corresponding parameter of the mapping specification of the measuring device is updated. This manner of proceeding is problematic to the extent that the behavior of a measuring device can also change in a manner such that it would require the correction of other parameters of the mapping specification, for example slope in the case of a linear mapping specification.

It is, therefore, an object of the present invention to provide a calibration method for measuring devices for overcoming the described disadvantages.

SUMMARY OF THE INVENTION

The object is achieved By a method for calibrating a measuring device monitoring a measured variable of a measured medium by means of at least a first sensor, whose signal is mapped to a measured value on the basis of a mapping specification, includes the steps of: recording a current, measured value of the measuring device as current calibration measured value; supplying to a laboratory reference measuring device a laboratory reference sample of the measured medium having the properties of the measured medium at the point in time of the recording of the calibration measured value; ascertaining with the laboratory reference measuring device the actual value of the measured variable on the basis of the laboratory reference sample and making available and storing the actual value as current laboratory reference measured value; updating the mapping specification on the basis of the current calibration measured value as well as the current laboratory reference measured value; and at least one, earlier value pair of a calibration measured value and an associated laboratory reference measured value, ascertained in an earlier calibration, is taken into consideration for updating the mapping specification.

Preferably, a plurality of earlier value pairs are taken into consideration for the updating of the mapping specification.

In a further development of the invention, also the point in time of measurement is recorded for the value pairs. This provides the opportunity for taking into consideration the age of the value pairs in the updating of the mapping specification. For example, age can enter as a weighting factor, according to which older value pairs have a lesser weight than younger value pairs. The relative weight of a value pair can, for example, be described using a decaying, exponential function of age.

Furthermore, the weight of an earlier value pair can decrease more rapidly to the degree that more current laboratory reference measured values lie in the vicinity of the earlier laboratory reference measured value.

Performance of a calibration can, on the one hand, be carried out periodically at predeterminable time intervals; on the other hand, a calibration can take place on the basis of the occurrence of an event—thus, under event control. To this end, the measuring device can have, for example, a dosimeter function, which registers load equivalents of the measuring device and integrates, for example, extreme temperatures, etc. A calibration can be required following consumption of a predeterminable loading allowance. In some regards, this function corresponds to a timescale weighted with loadings. In the case of lesser loadings, the device can be operated longer, until the next calibration, than in the case of higher loadings.

Finally, a calibration can be required when a measuring device outputs an unusual measured value. A measured value is, for example, unusual, when, at the measuring point in question, for a long time, no measured values have arisen in a predeterminable range of values about the current measured value and/or when, for a long time, no calibration has been performed in the predeterminable range of values.

The measuring device of the invention includes at least a first sensor for registering a measured variable of a measured medium, wherein the first sensor outputs a signal dependent on the measured variable; and an electronic circuit with a microcomputer, wherein the signal of the first sensor is mapped by the electronic circuit to a measured value on the basis of a mapping specification; and wherein the electronic circuit includes a data memory, in which value pairs of calibration measured values and associated laboratory reference measured values can be stored, in order to update the mapping specification on the basis of the value pairs.

The measuring device can be, for example, a measuring device for analysis of aqueous media, especially a turbidity measuring device for monitoring drinking water.

BRIEF DESCRIPTION OF THE DRAWINGS

The invention will now be explained on the basis of an example of an embodiment presented in the drawing, the figures of which show as follows.

DETAILED DISCUSSION

Figure 1:
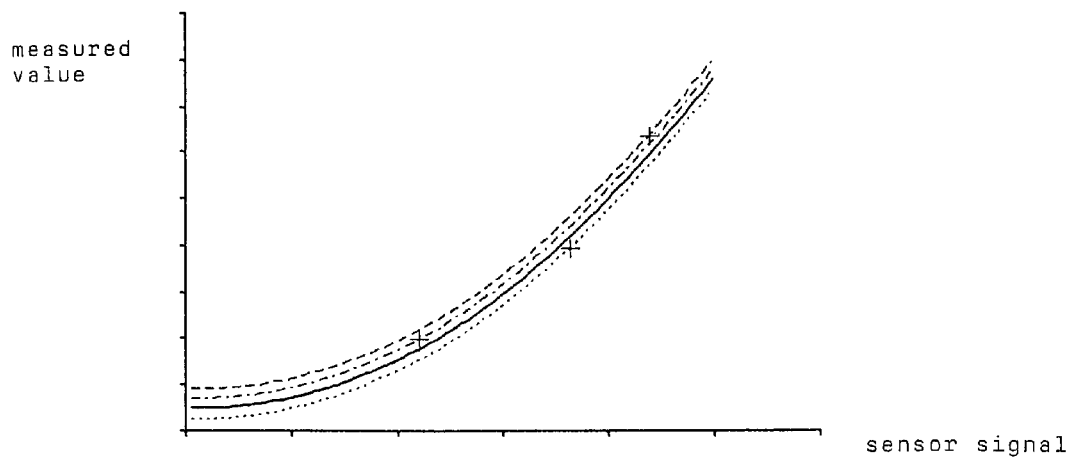
FIG. 1 is a diagram representing a state-of-the-art method of calibration with a laboratory reference.

FIG. 1 shows characteristic curves obtained by calibration using offset correction, such as is known from the state of the art.

The sensor signal is plotted on the horizontal axis, while the vertical axis shows the measured value for the measured variable of the sensor as a function of the sensor signal. The solid line in FIG. 1 corresponds to the characteristic curve of a measuring device at the point in time of its startup. Assume, in use of the measuring device, calibrations are performed periodically, for example monthly. At the point in time of the calibration, a calibration measured value is recorded with the current characteristic curve, and, simultaneously, a laboratory reference sample of the measured medium is taken. On the basis of the laboratory reference sample, a laboratory reference measured value is ascertained in the laboratory as desired value for the measuring device. As a result, then the zero-point, or offset, of the characteristic curve is shifted by the difference between laboratory reference measured value and calibration measured value, in order that the measured value to be output under the conditions of the current calibration corresponds to the desired value of the calibration. In order to indicate this, crosses are provided in FIG. 1 for different calibrations. In each case, the characteristic curve was shifted to the cross as a result of a calibration.

As immediately evident, there are large deviations between the output values as a function of the respectively applied characteristic curves, and the manner of proceeding according to the state of the art leads to errors in measurement, when other contributions than a zero-point shifting contribute to the drift of the measuring device.

Figure 2:
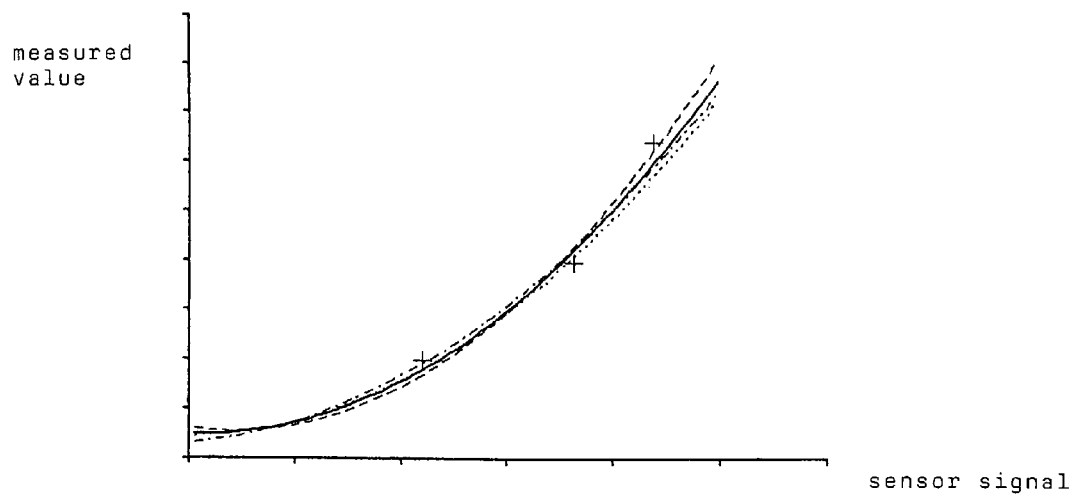
FIG. 2 is a diagram representing a method of the invention for calibrating with a laboratory reference.
Figure 3:
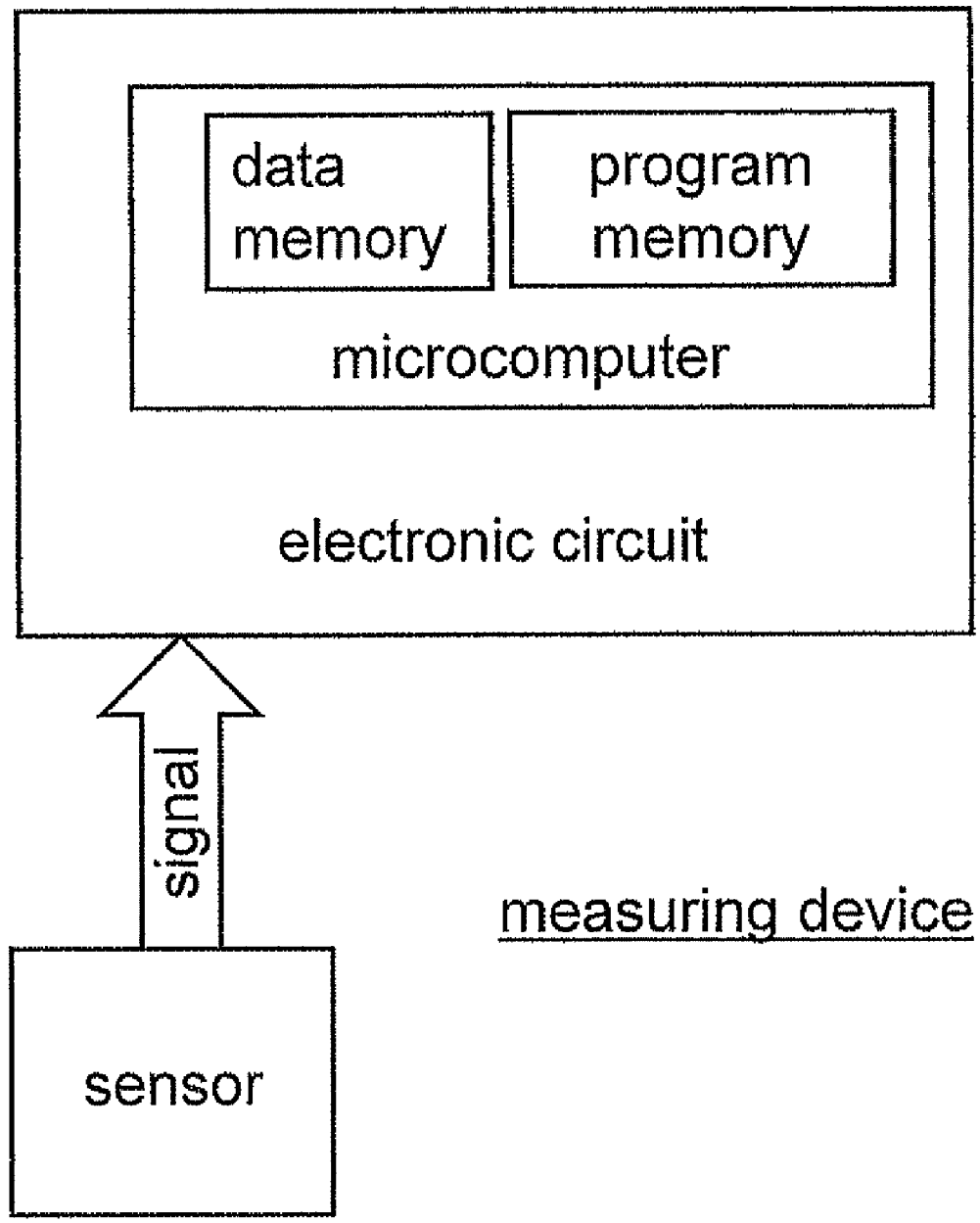
FIG. 3 is a schematic block diagram showing a measuring device, sensor, electronic circuit, data memory, and program memory to which the calibration method of the invention may be applied.

FIG. 2 shows characteristic curves for the laboratory reference method of the invention, wherein, for correction of the characteristic curves, not only the current calibration data are applied, but also earlier calibration data. The raw data in FIG. 2 are the same as the raw data of FIG. 1. I.e., the solid line is again the same characteristic curve for the point in time of startup.

The crosses show laboratory reference measured values of calibration data at three different points in time, where, it so happens, the point in time of calibration increases from left to right. This does not, however, have to be, since the position of the laboratory reference measured value in the diagram depends not on the point in time, but, instead, only on the calibration measured value, or the sensor signal of the calibration measured value, and the associated laboratory reference measured value.

In the example of an embodiment, in the case of the first calibration, the ascertained laboratory reference value was exactly so weighted as in the case of the original characteristic curve. I.e., a fit was performed for a polynomial of second order with 100 supporting points of the original characteristic curve and the value pair of the first calibration with 100-times weighting, in order to ascertain an updated characteristic curve. The result is presented as the dash-dotted line.

For ascertaining the characteristic curve for the second calibration, the value pair of the second calibration was taken into consideration at 100-times, the value pair of the first calibration at 50-times and the original characteristic curve with 100 supporting points in the case of a fit for a polynomial of second order, in order to ascertain a newly updated characteristic curve. The result is presented as the dotted line.

For ascertaining the characteristic curve for the third calibration, the value pair of the third calibration was taken into consideration at 100-times, the value pair of the second calibration at 50-times, the value pair of the first calibration at 25-times and the original characteristic line with 100 supporting points in the case of a fit for a polynomial of second order for the third updating of the characteristic curve. The result is shown as the dashed line.

One can see, immediately, that the relative deviations between the individual characteristic curves, especially in the case of the earlier calibration points, are markedly less. As a result, the method of the invention leads to a more robust updating of the characteristic curves. Equally, the original, factory calibration loses its relative significance as the number of subsequent calibrations increases, without, however, it being completely cast aside. This manner of proceeding is justified to the extent that certain basic characteristics of the device remain, even in the case of measured-value drift.

Instead of the described manner of proceeding for updating the characteristic curves, for example, also, in each case, the last characteristic curve, with a certain number of supporting points, can be fitted with a corresponding weighting of the current calibration data. In this way, the original characteristic curve loses significance more quickly.

Equally, the remaining difference between the new characteristic curve ascertained following a fit, relative to the laboratory reference value of the calibration, can be balanced by an additional offset of the characteristic curve.

Other statistical methods and strategies of analysis will be apparent to those skilled in the art on the basis of the ideas presented here, as a function of the aging behavior of the concrete measuring device and the relevant measuring point.

The invention claimed is:
1. A method for calibrating a measuring device monitoring a measured variable of a measured medium on the basis of at least a first sensor:
   providing a mapping specification on the basis of which a signal of the first sensor is mapped to a measured value of the measured variable;

recording at a point in time a current measured value of the measuring device as a current calibration measured value;

supplying to a laboratory reference measuring device a laboratory reference sample of the measured medium having properties of the measured medium which are the same as those at the point in time of the recording of the calibration measured value;

ascertaining with the laboratory reference measuring device an actual value of the measured variable on the basis of the laboratory reference sample and making available and storing the actual value as a current laboratory reference measured value;

wherein the calibration measured value and the current laboratory reference measured value are stored in a data memory of the measuring device;

updating the mapping specification based on the current calibration measured value as well as the current laboratory reference measured value by means of a program stored in a program memory of the measuring device; and at least one, earlier value pair of a calibration measured value and an associated laboratory reference measured value, ascertained in an earlier calibration and stored in the data memory of the measuring device, is taken into consideration for updating the mapping specification by the program.

2. The method as claimed in claim 1, wherein:
a plurality of earlier value pairs of calibration measured values and laboratory reference measured values are taken into consideration for updating the mapping specification.

3. The method as claimed in claim 1, wherein:
the age of the value pairs is taken into consideration in selecting weighting factors for updating the mapping specification, and older value pairs have lesser weight than younger value pairs.

4. The method as claimed in claim 1, wherein:
calibration is performed periodically.

5. The method as claimed in claim 1, wherein:
calibration is performed under event control.

6. A method as claimed in claim 1, wherein:
said mapping specification is represented in the form of a characteristic curve.

7. A method as claimed in claim 1, wherein:
said mapping specification is represented in the form of a linear equation or a polynomial.

8. A method as claimed in claim 7, wherein:
coefficients and/or a zero-point offset of said linear equation or said polynomial are stored in a data memory of the measuring device.

9. A measuring device, comprising:
at least a first sensor for registering a measured variable of a measured medium, wherein the first sensor outputs a signal dependent on the measured variable; and
an electronic circuit with a microcomputer having a data memory and a program memory, wherein:
the signal of the first sensor is mapped by the electronic circuit to a measured value based on a mapping specification;
the mapping specification is updateable, by recording at a point in time a current measured value of the measuring device as a current calibration measured value; supplying to a laboratory reference measuring device a laboratory reference sample of the measured medium having properties of the measured medium which are the same as those at the point in time of the recording of the calibration measured value; ascertaining with the laboratory reference measuring device an actual value of the measured variable on the basis of the laboratory reference sample and making available and storing the actual value as a current laboratory reference measured value, wherein the calibration measured value and the current laboratory reference measured value are stored in a data memory of the measuring device; updating the mapping specification based on the current calibration measured value as well as the current laboratory reference measured value by means of a program stored in a program memory of the measuring device; and at least one, earlier value pair of a calibration measured value and an associated laboratory reference measured value, ascertained in an earlier calibration and stored in the data memory of the measuring device, is taken into consideration of updating the mapping specification by the program; and
value pairs of calibration measured values and associated laboratory reference measured values can be stored in the data memory, and a program is stored in the program memory, in order to update the mapping specification on the basis of the value pairs.

10. The measuring device as claimed in claim 9, wherein:
said measuring device is a turbidity measuring device for monitoring drinking water.

* * * * *